United States Patent [19]
Meade et al.

[11] Patent Number: 5,540,705
[45] Date of Patent: *Jul. 30, 1996

[54] SUTURING INSTRUMENT WITH THREAD MANAGEMENT

[75] Inventors: John C. Meade, Walpole; Gerald I. Brecher, North Andover, both of Mass.

[73] Assignee: SuturTek, Inc., Boston, Mass.

[*] Notice: The term of this patent shall not extend beyond the expiration date of Pat. No. 5,437,681.

[21] Appl. No.: 445,359

[22] Filed: May 19, 1995

[51] Int. Cl.$^6$ ................................................. A61B 17/04
[52] U.S. Cl. ........................... 606/145; 606/139; 606/147
[58] Field of Search ............................ 606/139, 144–148

[56] References Cited

U.S. PATENT DOCUMENTS

| | | | |
|---|---|---|---|
| 2,327,353 | 8/1943 | Karle | 606/144 |
| 3,901,244 | 8/1975 | Schweizer | 606/144 |
| 4,440,171 | 4/1984 | Nomoto et al. | 606/144 |
| 4,462,395 | 7/1984 | Johnson | 606/144 |
| 4,484,580 | 11/1984 | Nomoto et al. | 606/144 |
| 4,596,249 | 6/1986 | Freda et al. | 606/144 |
| 5,152,769 | 10/1992 | Barber | 606/145 |
| 5,224,948 | 7/1993 | Abe et al. | |

FOREIGN PATENT DOCUMENTS

| | | |
|---|---|---|
| 0552430 | 3/1993 | European Pat. Off. |
| 4310315 | 11/1992 | Germany |

*Primary Examiner*—Gary Jackson
*Attorney, Agent, or Firm*—Cesari and McKenna

[57] ABSTRACT

A suturing instrument for suturing tissue comprises an elongated housing having opposite ends. A curved suturing needle having a pointed end and to which a suture is attached is supported at one end of the housing for rotational motion about an axis. A driver mechanism in the housing rotates said needle about said axis through successive revolutions. There may also be a suture tensioner in the housing which applies tension to the suture to draw the suture toward the other end of said housing following each revolution of said needle. In its operation, the instrument thus emulates the actions of a surgeon suturing manually.

13 Claims, 5 Drawing Sheets

SUTURING INSTRUMENT WITH THREAD MANAGEMENT

This invention relates to a suturing instrument. It relates more particularly to such an instrument which maintains positive control over the suturing needle and thread during the entire suturing process.

BACKGROUND OF THE INVENTION

Sutures are used in a wide variety of applications including closing ruptured or incized tissues, soft tissue attachment, anastamosis, attachment of grafts and mesh, etc. Conventionally, to suture ruptured or incized tissues, for example, a surgeon passes the pointed tip of a curved suturing needle with thread or suture attached to the blunt end of the needle through the tissues to be sutured until the tip of the needle penetrates the tissues to span the incision with the needle. Then, the surgeon grasps the tip of the needle which has been forced through the tissues with fingers or a needle holder and pulls the needle through the tissues, the suture following the curved path of the needle. Usually a knot or button is present at the trailing end of the suture to anchor the first stitch. After the surgeon has pulled the suture entirely through the tissues to tension the first stitch, he or she then forces the tip of the needle through the tissues at a location spaced along the incision from the first stitch until the needle again spans the incision. Again, he grasps the tip of the needle which has been forced through the tissues, applies tension to the needle pulls the entire suture through the tissues to complete the second stitch. This process is repeated again and again, with the surgeon tensioning the suture after each stitch to draw the tissues together thereby creating a running or continuous stitch, composed of individual thread loops, which extends the entire length of the incision or rupture.

Needless to say, such suturing by hand is a tedious and time consuming task. Moreover, it involves the repeated handling of the pointed needle, often in very close quarters. In many cases, this results in the needle penetrating the surgeon's gloves raising the possibility of infection for the patient and/or the surgeon.

To address these problems, some suturing instruments have been designed which are supposed to facilitate the manipulation of the suturing needle during the suturing process. See, for example, U.S. Pat. Nos. 2,959,172; 4,109,658; 4,345,601 and 4,557,265. However, to applicants' knowledge, such instruments are not in widespread use. Some of them are unduly complicated and, therefore, expensive. Other prior instruments are relatively difficult to use and are, therefore, not suitable for suturing of a delicate nature and/or in close quarters. For example, the instrument disclosed in the last-mentioned patent above has to be held sideways relative to the direction of the incision being closed. Some of the prior suturing devices suffer also because they do not maintain positive control over the suturing needle and thread during the suturing process. This can result in a non-uniform suture having overly loose and/or overly tight stitches which can cause excessive bleeding and/or tearing of tissue.

In general, the prior instruments of this general type are seriously disadvantaged because they do not emulate the manual suturing techniques preferred by surgeons that enable the surgeons to "tailor" each suture to the particular situation and they do not even attempt to handle or manage the thread during the suturing process so as to optimize that process.

SUMMARY OF THE INVENTION

Accordingly, the present invention aims to provide an improved suturing instrument.

Another object is to provide such an instrument which emulates on replicates the manual suturing actions carried out by surgeons.

Another object of the invention is to provide a suturing instrument which maintains positive control over needle movement during all phases of the suturing process.

Still another object is to provide an instrument of this type which maneuvers the suturing material through a tissue incision in more or less the same way a surgeon would do by hand.

A further object of the invention is to provide a suturing instrument which incorporates a unique thread management system which controlledly pulls the thread entirely through the patient's tissues following each stitch.

Yet another object of the invention is to provide a suturing instrument which is relatively easy to operate using only one hand.

A further object of the invention is to provide an instrument of this type whose working end is formed as a disposable cartridge.

Another object of the invention is to provide a suturing instrument which can be configured as to length and tip size for use in conventional open surgery as well as in minimally-invasive surgery (MIS).

Still another object of the invention is to provide a hand-held suturing instrument of relatively simple mechanical construction and which requires no external motive source.

A further object is to provide a suturing instrument which eliminates the need for needle holders and other tools normally required for suturing.

Other objects will, in part, be obvious and will, in part, appear hereinafter.

The invention accordingly comprises the features of construction, combination of elements and arrangement of parts which will be exemplified in the following detailed description, and the scope of the invention will be indicated in the claims.

Briefly, our surgical suturing instrument is shaped more or less like a pistol in that it includes a barrel with a hand grip extending from the proximal end of the barrel. Releasably mounted to the distal end of the barrel is a disposable cartridge which houses the suturing needle and thread.

The disposable cartridge has a generally cylindrical housing with an aperture in the sidewall of the housing at the distal or working end thereof. Slidably mounted in a circular track at the distal end of the housing opposite the aperture is an arcuate suturing needle having a pointed tip at one end of the needle. The needle is connected to one end of a suturing thread contained in the cartridge. The circumference of the suturing needle is more or less equal to the circumference to the cartridge housing at the aperture therein and the needle normally reposes in a home position in its track such that the gap in the arcuate suturing needle is in register with the aperture in the cartridge housing. In other words, the pointed tip of the needle is situated in one side of the housing aperture and the blunt end of the needle attached to the suturing thread is located at the opposite side of the aperture.

In accordance with the invention, the needle may be releasably engaged by a driver rotatably mounted in the barrel of the instrument so that the needle can be rotated from its home position 360° about the cartridge axis. This causes the tip of the needle to advance across the cartridge housing aperture so that the needle spans the aperture. Thus, when the instrument is positioned so that the tissues to be sutured are situated at the housing aperture, the needle will penetrate the tissues and span the incision between them. Continued rotation of the needle to return it to its original or home position will pull the thread attached to the needle down through the tissue on one side of the tissue incision and up through the tissue on the opposite side of the incision. Thus, the suture follows the curved path of the needle to tie the tissues together with a stitch of thread exactly as it would do if a surgeon were suturing manually. Preferably, anchoring means are provided at the trailing end of the suture to prevent the suture from being pulled completely through the tissue.

The instrument may then be advanced a short distance along the incision and the needle driven through another 360° rotation to produce the second stitch of the suture. As will be seen, the instrument automatically pulls the entire suture through the tissues under controlled tension, exactly as a surgeon would do manually so as to tighten the stitch without tearing tissue.

The surgeon continues to manipulate the instrument, alternately advancing and rotating the needle about an axis that is generally parallel to the direction of advancement to create a continuous suture which may extend the entire length of the incision. After each individual stitch is laid down, it is tightened so that the resultant suture is neat and tensioned uniformly along its length. Therefore, bleeding and tearing of tissue are minimized.

As will be described in detail later, the needle driver may be operated by the surgeon holding the instrument with one hand using the thumb of that hand. For this, the instrument includes a thumb-operated lever located near the instrument's hand grip and internal gearing to enable the surgeon to efficiently and effectively lay down a running stitch to close the tissue incision in a minimum amount of time.

Our instrument may also include an associated thread management system which operates in conjunction with the needle driver to control or handle the suturing thread so as to pull the thread entirely through each stitch to tighten the stitch without damaging tissue, again emulating the action of the surgeon when suturing by hand. The thread management system may also be operated by means of the instrument's thumb-actuated lever so that the instrument controllably pays out the suturing thread during the suturing process. Thus, there is minimal liklihood of the thread becoming tangled or hung up during the suturing operation.

When using the present instrument, no ancillary instruments or tools such as needle holders, forceps or the like are needed to complete the suture. Also, the instrument may be made in various configurations for use in open surgery to perform procedures such as closing of the fascia, skin closure, soft tissue attachment, anastamosis, fixation of mesh, grafts and other artificial materials; it may also be designed with a very small working end or tip at the end of a long rigid or flexible shaft so that the instrument may be used for MIS, such as suturing in the course of endoscopic surgery, including laparoscopy, thorascoscopy and arthroscopy.

Despite having all of the advantages discussed above, the present instrument is relatively easy and inexpensive to manufacture. Furthermore, it can be operated quite easily using only one hand. Therefore, it should find wide application wherever sutures consisting of single stitches or continuous stitches, e.g. spiral, mattress, purse string etc. are required to close tissue incisions or to attach grafts or the like.

BRIEF DESCRIPTION OF THE DRAWINGS

For a fuller understanding of the nature and objects of the invention, reference should be had to the following detailed description, taken in connection with the accompanying drawings, in which.

DETAILED DESCRIPTION OF ILLUSTRATIVE EMBODIMENT

Figure 1:
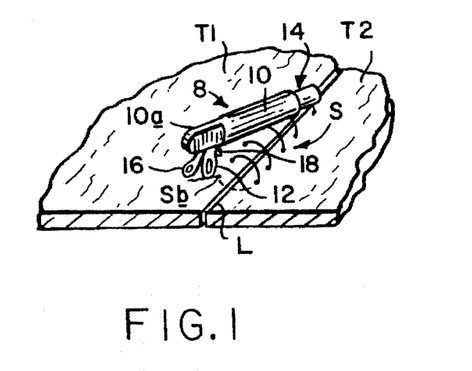
FIG. 1 is a diagrammatic view showing a suturing instrument incorporating our invention being used to suture a tissue incision.

Referring to FIG. 1 of the drawings, our suturing instrument may be used to produce a continuous stitch or suture S to close an incision L between two tissues $T_1$ and $T_2$. The instrument includes an actuator shown generally at 8 which is shaped like a pistol in that it has a generally cylindrical barrel 10 with a hand grip 12 extending from a housing 10a at the proximal end of the barrel. The instrument also includes a disposable suturing needle-and-thread cartridge 14 releasably plugged into the distal end of barrel 10. The instrument is used by positioning the distal or working end of cartridge 14 against the tissues $T_1$ and $T_2$ to be sutured with the instrument pointing generally in the direction of the incision L. The surgeon, using only one hand, may manipulate the instrument while actuating a lever 16 and a trigger 18 at the base of housing 10a to close the incision L with a continuous suture S whose stitches may be individually tensioned precisely and uniformly along the length of the suture exactly as would occur if a surgeon were suturing by hand in the conventional way. Usually, the surgeon would employ a single suture S which would extend the entire length of incision L.

Figure 2:
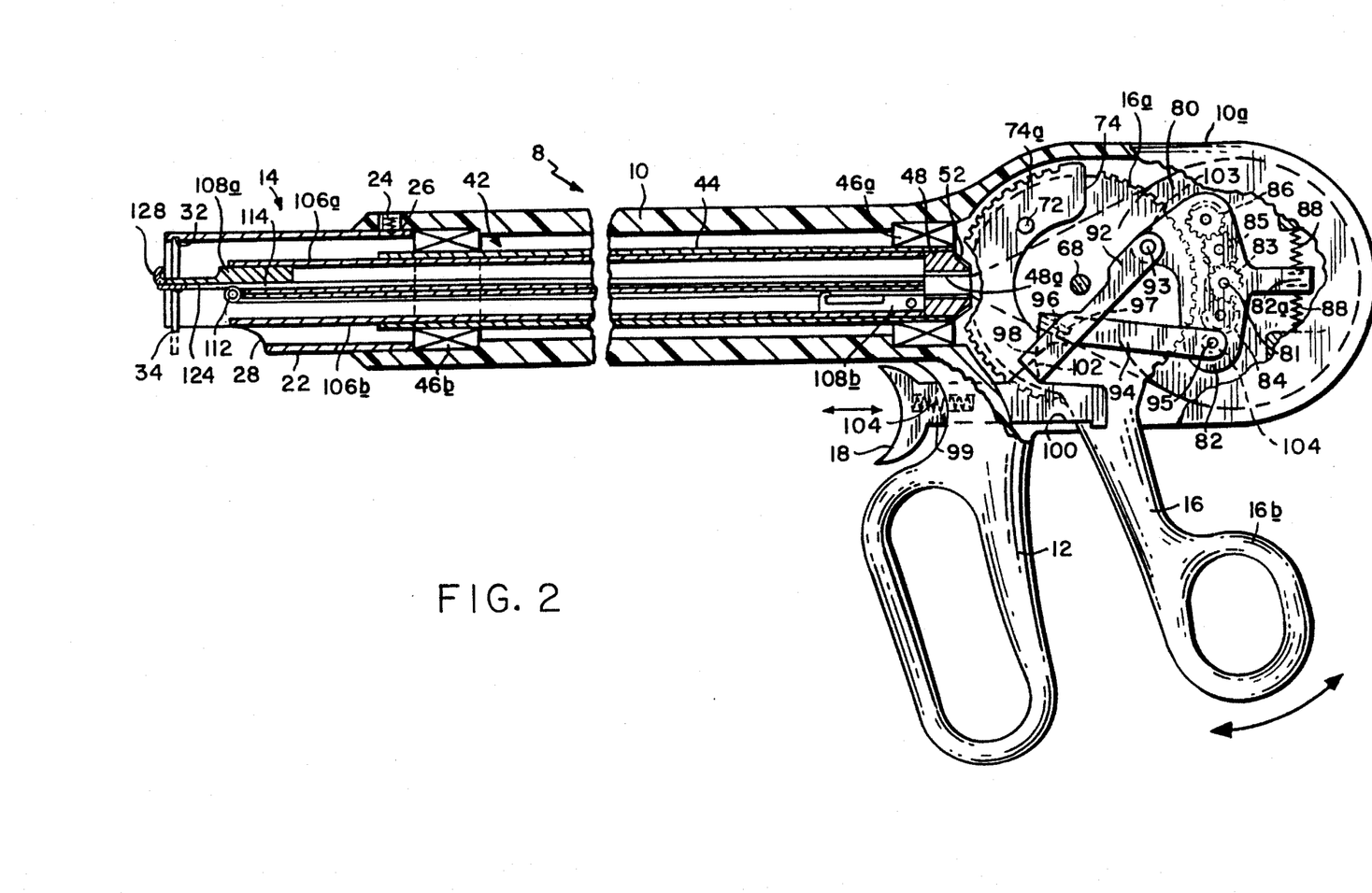
FIG. 2 is a side elevational view on a much larger scale and with parts broken away showing the elements of the FIG. 1 instrument in greater detail.
Figure 3:
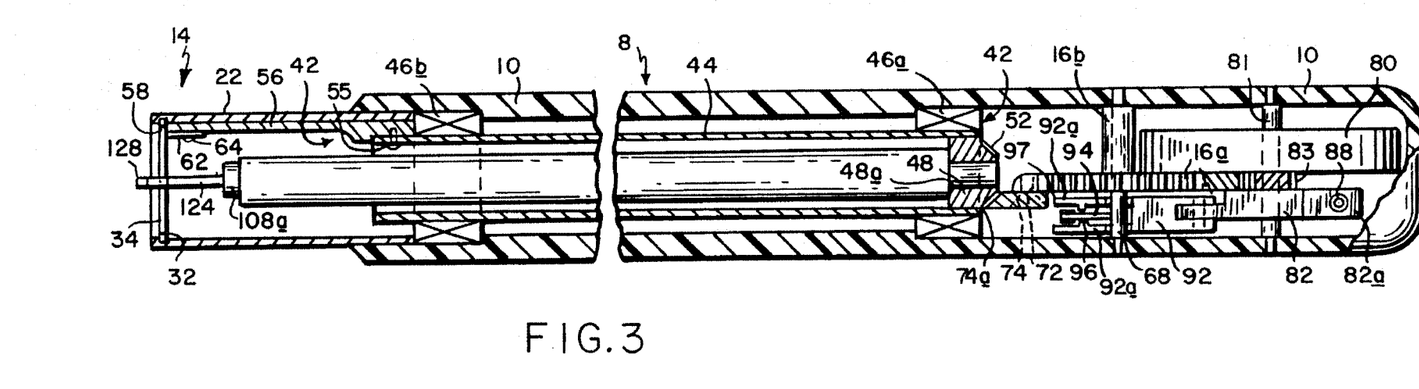
FIG. 3 is a longitudinal section with parts in elevation of the FIG. 1 instrument.

Turning now to FIGS. 2 and 3, the barrel 10 of actuator 8 comprises a generally cylindrical tube whose proximal end is connected to the housing 10a. The instrument grip 12 extends down from the undersides of the barrel and housing. Preferably, the grip 12 is in the form of a ring as shown so that the user's fingers can be inserted through the grip to enable a firm grasp of the instrument.

Figure 5B:
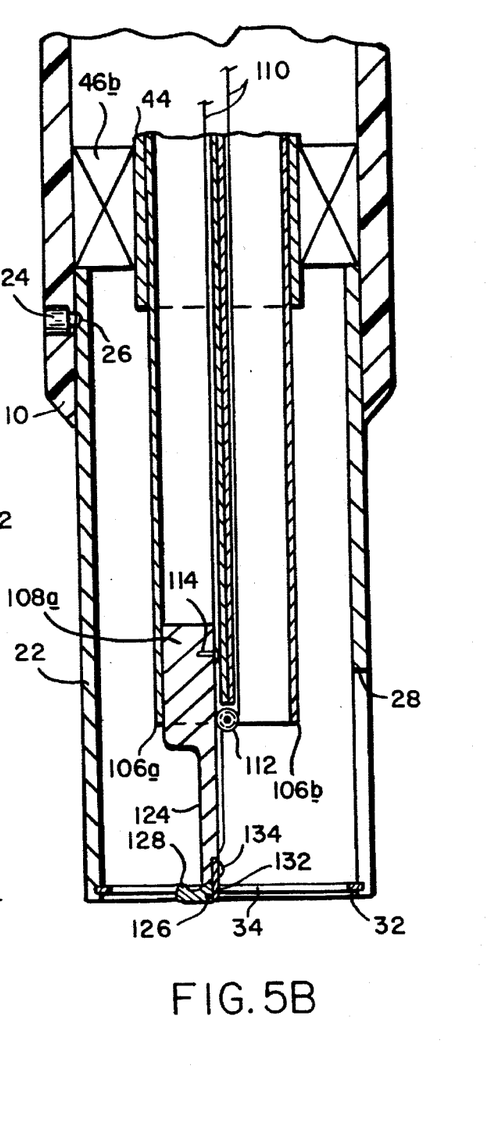
FIG. 5B is a fragmentary side elevational view of that end.
Figure 6A:
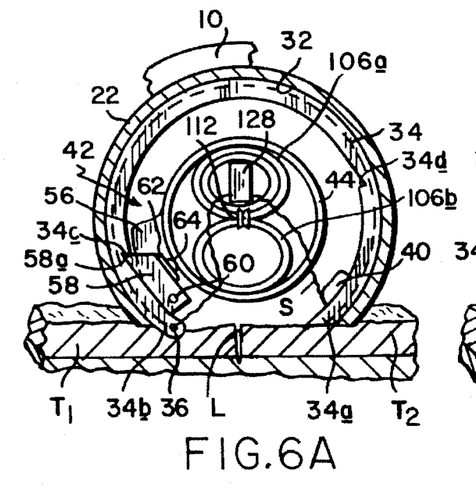
FIGS. 6A to 6I are sectional views taken along line 6—6 of FIG. 5A, illustrating the operation of the instrument.

The disposable cartridge 14 is preferably offered in a sterilized sealed pouch; see pouch 40 in FIG. 6A. The cartridge comprises a generally cylindrical tubular housing 22 which may be formed of a suitable rigid, medical grade, sterilizable metal or plastic material. Housing 22 may be releasably retained in the distal end of barrel 10 by known means such as a spring button 24 mounted in barrel 10 and adapted to engage in a dimple 26 formed in the side wall of cartridge housing 22, as best seen in FIGS. 2 and 5B. The spring button 24 fixes both the longitudinal and rotational positions of the cartridge 14 in the barrel 10.

Figure 5A:
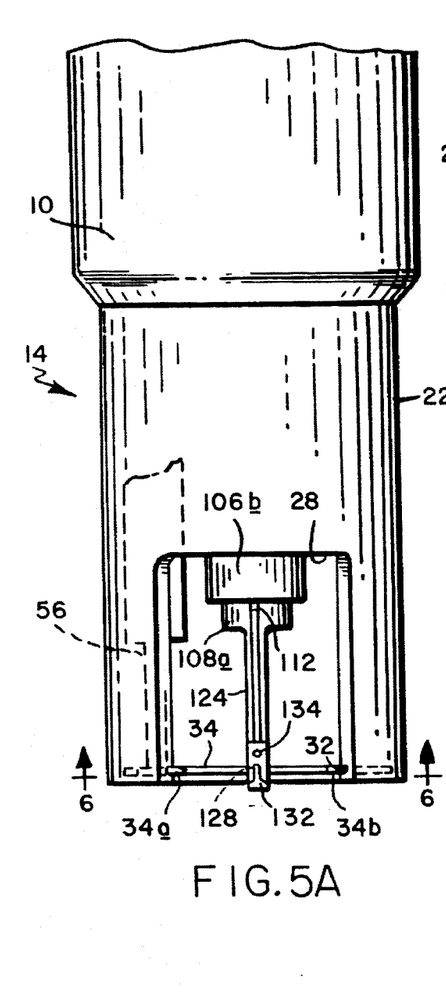
FIG. 5A is a fragmentary bottom view on a still-larger scale showing the working end of the FIG. 1 instrument.

Referring to FIGS. 2, 5A and 5B, an aperture 28 is formed in the underside of the cartridge housing 22 at the distal end of the cartridge. Also, a circular groove or track 32 is inscribed in the inside surface of housing 22 at the distal end thereof, which track lies in a plane that is perpendicular to the longitudinal axis of the housing 22 and of the instrument as a whole. Thus, as best seen in FIG. 5A, the track 32 is interrupted by the aperture 28. Slidably positioned in the groove or track 32 is a curved medical grade stainless steel suturing needle 34. The illustrated needle is formed as a circular split ring, one end 34a of which is pointed. The needle also contains an opening or eye 36 by which the leading end of suture S may be attached to the needle. In the illustrated instrument the eye 36 is located adjacent to the blunt end 34b of the needle. However, it could just as well be positioned anywhere along the arc of the needle between the apex and end 34b as shown at 36' in FIG. 6I. To enable the needle to penetrate tissue to the required depth, the needle should have an arcuate extent between 180° and 330°, 330° being preferred.

The width of the aperture 28 in the cartridge housing 22 is comparable to the width of the gap in needle 34 so that when the needle is positioned at a home position as shown in those figures, it does not project materially into the aperture 28, i.e., it may project slightly. The needle 34 may be rotated in its curved track 32 about the instrument's longitudinal axis to advance the pointed needle tip 34a so that the needle first spans the aperture 28 as shown, for example, in FIG. 6B and then returns to its original or home position illustrated in FIGS. 5A and 6A. Since the suture S is attached to needle 34, the suture follows the path of the needle. The suture may be stored initially in a small pouch 40 adhered to the inside surface of cartridge housing 22 and be pulled out of that pouch during the first two stitches of the suturing process as will be described later. Alternatively, it may be arranged in a festoon releasably adhered to the inside surface of cartridge housing 22.

Referring now to FIGS. 2 and 3, the needle 34 is rotated about the axis of cartridge 14 by a driver mechanism shown generally at 42. While the mechanism 42 may take a variety of forms, the illustrated one comprises a tubular shaft 44 which is rotatably mounted coaxially in barrel 10 by means of bearing units 46a and 46b located adjacent to opposite ends of shaft 44. The proximal end of shaft 44 is closed by a tubular plug 48 having an axial passage 48a and an exposed end surface formed as a bevel gear 52. The distal end of shaft 44 which projects beyond the bearing unit 46b is connected at one side by pins 55 to a straight leg 56 which extends from the end of barrel 10 along the cartridge housing 22 to the needle track or groove 32 therein.

As best seen in FIGS. 2 and 6A, a pawl 58 is connected at one end by a pivot pin 60 to the free end of leg 56 radially inboard needle 34. The opposite or free end of pawl 58 is cut to form a sharp outside edge 58a. That pawl edge 58a is arranged to engage in a pair of notches 34c and 34d in the radially inner edge of needle 34 and located adjacent to the opposite ends of the needle. Preferably, the notches are spaced about 180° apart around the needle. Pawl 58 is biased outward toward the needle 34 by a leaf spring 62 fastened by pins 64 to the radially inner surface of leg 56. Thus, when drive shaft 44 is rotated about its longitudinal axis in the clockwise direction as viewed in FIG. 6A, pawl 58 will engage in notch 34c or 34d so as to advance needle 34 in the same direction. On the other hand, when shaft 44 is rotated in the opposite or counter clockwise direction, there is no engagement of the needle by the pawl 58 so that the needle will not be moved counter clockwise by shaft 44.

Figure 6B:
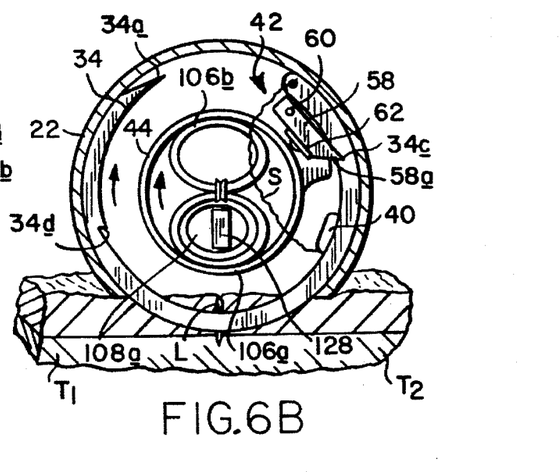

As will be described in more detail later, with the pawl 58 engaged in the needle notch 34c, when the drive shaft 44 is at a home position shown in FIG. 6A, shaft 44 may be rotated from that position approximately 180° so as to rotate needle 34 from its home position by the same amount; see FIG. 6B. This places the needle notch 34d at the location formerly occupied by notch 34c. Shaft 44 may then be turned in the opposite direction to its original position whereupon pawl 58 will engage in the needle notch 34d; see FIG. 6C. Shaft 44 may then be rotated in the original direction again through 180° carrying needle 34 along with it so that the needle is returned to its original or home position; see FIG. 6D.

Referring again to FIGS. 1 and 2, the drive shaft 44 is rotated by moving the lever 16 which extends down from the actuator housing 10a. Lever 16 is pivotally mounted by an axle 68 to the opposite side walls of housing 10a at a location on the longitudinal axis of the instrument. The upper end of lever 16 is formed as a relatively large diameter spur gear 16a with a tubular hub 16b which is rotatably engaged on axle 68 inside housing 10a. Fastened to the inboard face of gear 16a forward of axle 68 by means of threaded fasteners 72 is a flat bevel gear segment 74 having a beveled edge 74a which more or less follows the curvature of the spur gear 16a. That edge meshes with the bevel gear 52 at the proximal end of drive shaft 44. Thus, when the lever 16 is moved rearwardly away from grip 12, the drive shaft 44 and the leg 56 attached to that shaft will be moved about the instrument's axis in the clockwise direction as viewed in FIG. 6A. On the other hand, when the lever 16 is moved in the opposite direction toward the finger grip 12, shaft 44 and leg 56 will be rotated in the counter clockwise direction about that axis. In actual practice, the surgeon holding the instrument by means of the grip 12 will move lever 16 back and forth by means of the thumb as is done with the thumb ring on some forceps. For this reason, a thumb ring 16b is provided at the free end of the lever 16.

Also positioned inside housing 10a behind axle 68 is a spool or drum 80 which rotates with an axle 81 journalled in the opposite sidewalls of the housing. A pinion 83 also rotates with axle 81 opposite drum 80. Rotatably mounted on axle 81 is a bracket 82 which can pivot independently of the axle and pinion 83.

Pinion 83 meshes with a driver pinion 84 rotatably mounted to the inboard face of bracket 82 and with an idler pinion 85 also rotatably mounted to that bracket. The idler pinion meshes, in turn, with another driver pinion 86 also rotatably mounted to bracket 82. Thus, all of the pinions 83 to 86 form a gear train.

Bracket 82 is free to pivot or rock on axle 81 between two positions. In one of these positions, pinion 84 meshes with gear 16a in housing 10a; the other position brings pinion 86 into meshing engagement with that gear 16a. Bracket 82 is biased toward a neutral position shown in FIG. 2 wherein both pinions 84 and 86 are spaced away from gear 16a by opposing springs 88 compressed between an arm extension 82a of bracket 82 and inwardly projecting bosses 89 on the housing 10a sidewalls.

Bracket 82 is moved between its two positions by a trigger mechanism which is actuated by trigger 18. This mechanism includes a first link 92 having one end connected by a pivot pin 93 to the upper end of bracket 82 and a second link 94 connected at one end by a pivot pin 95 to the lower end of that bracket. Both links extend forwardly toward trigger 18.

As shown in FIG. 3, link 92 is formed with a pair of spaced-apart, parallel, forwardly extending arms 92a having a pair of opposed inwardly extending bosses 96 near the free forward ends of those arms. Link 94, on the other hand, has a pair of inclined ramps 97 projecting laterally from opposite sides at the upper forward corner of that link and a depending wedge-shaped nose 98 at the lower forward corner of that link. Link 94 is made thin enough to slidably fit into the space between the arms 92a and 92b of link 92 such that the ramps 97 may be disposed either on or under the bosses 96 of link 92.

Referring to FIGS. 2 and 3, trigger 18 has a rearwardly extending arm 99 which is slidably positioned in a longitudinal slide 100 formed in housing 10a near the top of grip 12. Arm 99 extends under the free ends of links 92 and 94 and an upwardly projecting wedge-shaped pawl 102 is formed on the arm adjacent to those link ends. Trigger 18 is biased toward a forward position by a spring 104 compressed between trigger 18 and the housing 10a so that the pawl 102 engages in front of either the link 92 (see FIG. 4A) or the nose 98 of link 94 (see FIG. 4C). The links 92 and 94 are biased toward arm 99 (i.e. counterclockwise) by torsion springs 103 and 104, respectively, (FIG. 2).

The trigger mechanism just described for pivoting bracket 82 constitutes part of the means for managing or handling the suture material when the instrument is being used. The function of the mechanism is to rotate drum 80 in opposite directions using lever 16 upon successive actuations of trigger 18.

Figures 4A, 4B:
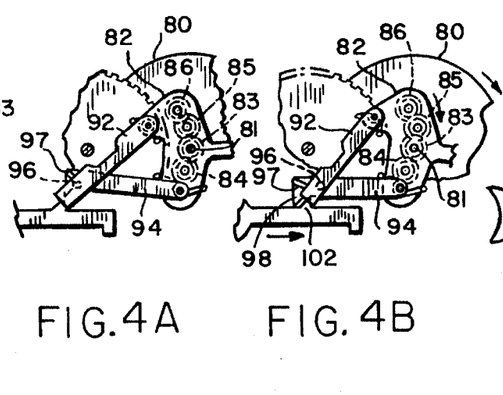
FIG. 4A to 4E are diagrammatic views illustrating the operation of a portion of the FIG. 1 instrument.

More particularly and referring to FIGS. 2 and 4, when the trigger 18 is in its normal forward position, assume that the pawl 102 on trigger arm 99 engages in front of link 92 as shown in FIGS. 2 and 4A. In this position, the bosses 96 on link 92 are located under ramps 97 on link 94 so that link 94 is elevated above trigger arm 99. If trigger 18 should be squeezed, the trigger arm pawl 102 will be urged rearwardly and push against link 92 thereby rocking bracket 82 clockwise about axle 81 to the position shown in FIG. 4B wherein pinion 84 meshes with gear 16a. Also, as soon as bosses 96 on link 92 clear the ramps 97 on link 94, link 94 will drop down so that the link nose 98 rides on trigger arm 99 in front of pawl 102 as shown in that figure.

If now the lever arm 16 is swung forwardly, gear 16a will be rotated clockwise as viewed in FIGS. 2 and 4. Since pinion 84 is now in mesh with that gear, that pinion will rotate pinion 83, as well as axle 81 and drum 80, clockwise as shown in FIG. 4B.

Figure 4C:
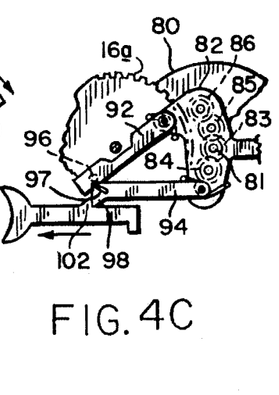

When trigger 18 is released, the trigger and its arm 99 will return to the forward position as shown in FIG. 4C so that the pawl 102 on arm 99 slides under links 92 and 94 and comes to rest in front of link 94. Also, springs 88 will bias bracket 82 counter clockwise to its neutral position thereby disengaging pinion 84 from gear 16a. This movement of that bracket pushes link 92 forwardly and pulls link 94 rearwardly causing the bosses 96 on the former link to ride up on the ramps 97 of link 94 thereby jacking up the link 92 to the position shown in FIG. 4C so that the free end of the link is spaced above pawl 102 on trigger arm 99.

Figures 4D, 4E:
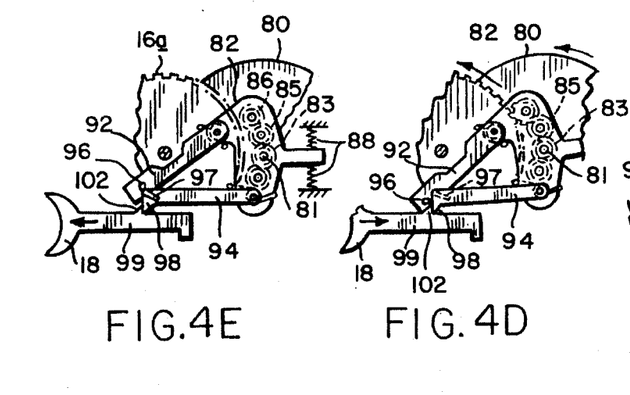

The next time the trigger 18 is squeezed, the pawl 102 on trigger arm 99 will exert a rearward force on the forward end of link 94 causing bracket 82 to pivot counter clockwise about axle 81 so that pinion 86 meshes with gear 16a as shown in FIG. 4D. Now, if lever 16 is moved forwardly, this will pivot gear 16a clockwise. Consequently, that gear, acting through the pinions 86 and 85, will cause pinion 83 and thus drum 80 to rotate in the counter clockwise direction as shown in FIG. 4D. Also, the bosses 96 on link 92 will clear the forward ends of ramps 97 on link 94 allowing the former link to drop down onto arm 99 in front of pawl 102 as seen in that figure.

As shown in FIG. 4E, when the trigger 18 is released, it will return to its forward position. Also, bracket 82 will return to its neutral position disengaging pinion 86 from gear 16a. This will locate the links 92 and 94 at the same positions they had initially in FIG. 4A so that pawl 102 is again positioned in front of link nose 98 and bosses 96 of link 92 rest on ramps 97 of link 94. It should be obvious that the next time trigger 18 is squeezed, drum 80 will be rotated counter clockwise again. Thus, each time trigger 18 is squeezed and lever 16 is moved forwardly, drum 80 will be rotated alternately in opposite directions.

Referring now to FIGS. 2, 3 and 5B, the rest of the thread management means referred to above comprises suture encagement means in the form of a pair of tubes 106a and 106b which extend within the tubular drive shaft 44 the entire length of that shaft and beyond, almost to the distal end of cartridge 14. Preferably, the tubes 106a and 106b are fastened within the drive shaft 44 such that when the drive shaft is in its home position as shown in FIGS. 2 and 6A, the tubes are situated one over the other and in line with the aperture 28 in cartridge wall 22.

Tubes 106a and 106b function as guides for suture engagement means comprising a pair of shuttles 108a and 108b which are movable between the proximal and distal ends of their respective tubes. The shuttles are moved by means of a wire loop 110 which is stretched between the drum or pulley 80 and a much smaller pulley 112 rotatably mounted at the distal ends of tubes 106a and 106b such that one stretch of the wire loop extends from the drum 80 through the passage 48a in plug 48 and down through tube 106a to pulley 112 and the other loop stretch extends from pulley 112 through tube 106b, through plug passage 48a and back to the drum 80. Preferably, there are several turns of wire around the drum to prevent slippage.

The shuttles 108a and 108b are adjustably connected to the wire passing through tubes 106a and 106b by means of pinch screws 114 which clamp the wire to the shuttles. By moving the wire loop 110 in one direction or the other, shuttles 108a and 108b may be moved between extended and retracted positions within their respective tubes 106a and 106b.

When a particular shuttle, say shuttle 108a, is in its extended position, it projects somewhat beyond the distal end of its tube 106a as shown in FIG. 2. On the other hand, when that shuttle is in its retracted position, it is positioned at the proximal end of its tube adjacent to the plug 48; see shuttle 108b in that figure. The wire loop 110 is moved by squeezing trigger 18 which engages either pinion 84 or 86 with gear 16a and moving lever 16 forwardly toward grip 12. Preferably, the shuttles 108a and 108b are secured to the wire loop 110 so that when one shuttle is in its extended position, the other shuttle is in its retracted position. Thus, for example, to move the shuttle 108a to its extended position and shuttle 108b to its retracted position as shown in FIG. 2, the surgeon should squeeze trigger 18 to engage gear 16a with pinion 86 and move lever 16 forwardly. This will rotate the drum 80 in the counter clockwise direction (FIG. 2) thereby moving wire loop 110 so that it advances shuttle 108a to the distal end of tube 106a and pulls shuttle 108b to the proximal end of tube 106b. The next time the trigger is squeezed and lever 16 is moved forwardly toward grip 12, shuttle 108a will be retracted and shuttle 108b will be extended.

Refer now to FIGS. 5A and 5B which show the shuttle 108a in greater detail. Shuttle 108b is identical to shuttle 108a. As shown in those figures, each shuttle includes a generally cylindrical main body 122, having a pinch screw 114 at its proximal end for securing that shuttle to the wire loop 110. A narrow hook leg 124 extends from the distal end of main body 122 at the inboard side of the body. When the shuttle 108a is in its extended position as shown in those figures, the free end of leg 124 intercepts the plane of needle 34. Connected by a pivot pin 126 to the free end of finger 124 is a short curved hook leg 128. Also, positioned adjacent to leg 128 is a leaf spring 132 one end of which is secured to the back of leg 124 by a pin 134. The opposite or free end of leaf spring 132 engages the side edge of hook leg 128 which functions as a cam surface to normally maintain that leg in a laterally extended position as shown in FIGS. 5A and 5B. However, an axial force on the hook leg 128 of a selected magnitude that overcomes the bias of spring 132 will pivot that hook leg about pin 126 so that that leg lies parallel to leg 124 allowing a hooked suture to be released from the hook as will be described shortly. Of course, the dimensions and shape of the hook leg 128 are such that the hook can be retracted into the associated tube 106a. Preferably, each shuttle is secured to the wire loop 110 so that its hook leg 128 faces upwards as shown in FIGS. 2 and 5. The tension on the wire loop 110 maintains the proper orientations of the shuttles. Alternatively, the tubes 106a, 106b and shuttles 108a, 108b may have non-circular cross sections to maintain the orientations.

The function of the shuttles is to engage the suture S following each stitch and to pull the entire suture through the stitch under a controlled amount of tension as a surgeon would do when suturing manually and to store the suture in either tube 106a or 106b in preparation for the next stitch. The operation of the shuttles will be described in detail presently in connection with FIGS. 6A to 6I.

Referring now to FIGS. 1 and 6A, in order to use the instrument, a fresh cartridge 14 is plugged into the distal end of the actuator 8. In each cartridge, the needle 34 is set initially in its home position illustrated in FIG. 6A with the suture S attached to the needle end 34b being stored in pouch 40. When the cartridge is installed in the actuator, the suture is engaged around the hook 128 of the extended shuttle, e.g., shuttle 108a in FIGS. 2 and 6A. Also, the lever 16 is moved to its forward position so that the driver mechanism 42, including foot 56, is located at the home position as shown in FIG. 6A such that the pawl 58 is engaged in the needle notch 34c adjacent to the rear end 34b of the needle 34.

Next, the instrument is positioned as shown in FIGS. 1 and 6A so that the distal end of the cartridge 14 engages the tissues $T_1$ and $T_2$ to be sutured at aperture 28, with the instrument pointing in the direction of the tissue incision L. With the instrument in this position, the tissues $T_1$ and $T_2$ bridge the aperture 28 of cartridge 14 such that the tissues intercept the circular motion path of the needle 34.

To commence suturing, the surgeon, holding the instrument by means of the grip 12, moves lever 16 rearwardly with the thumb without squeezing trigger 18. Under these conditions, the bevel gear segment 74 engaged to bevel gear 52 will rotate the drive shaft 44 and foot 56 clockwise as viewed in FIG. 6A so that needle 34, which is engaged by the pawl 58, will rotate with the shaft approximately 180° to the position shown in FIG. 6B. This motion of the needle causes the needle tip 34a to penetrate down through the tissue $T_2$ and up through the tissue $T_1$ following a curved path as shown in FIG. 6B.

Figure 6C:
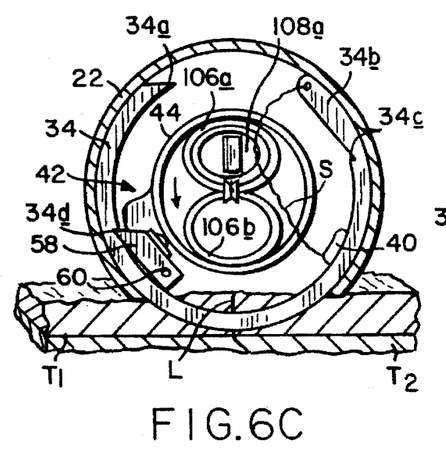

At this point, the surgeon moves the lever 16 forwardly so as to rotate the drive shaft 44 and the attached foot 56 in the opposite or counter clockwise direction to the position shown in FIG. 6C until the pawl 58 snaps into the needle notch 34d which is now situated at substantially the same location formally occupied by notch 34c.

Figure 6D:
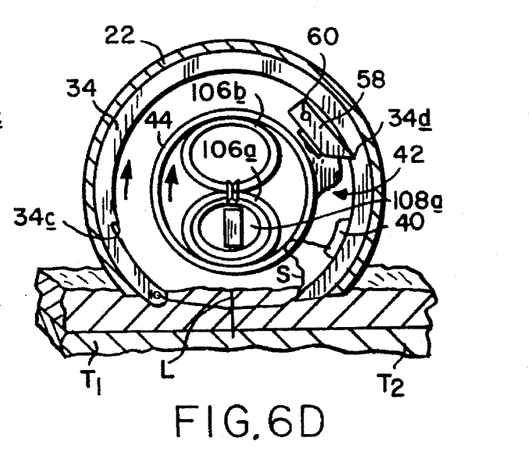
Figure 6E:
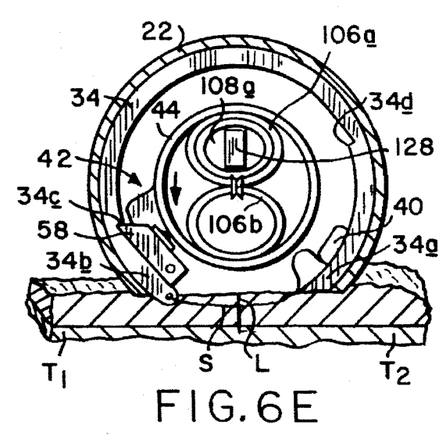

Next, the surgeon moves lever 16 rearwardly again so as to rotate the drive shaft 44 and foot 56 clockwise through 180° to the position shown in FIG. 6D. This motion of the drive shaft moves the needle through an additional 180° so that it advances completely through the tissues $T_1$ and $T_2$ and returns to its original or home position. In doing this, the needle pulls the leading end of the suture S along the same path through the tissues as shown in FIG. 6D, the suture being paid out from pouch 40. Thus, the needle 34 behaves in the same way as a conventional suturing needle wielded by a surgeon. The surgeon may then move lever 16 to its forward position to rotate the drive shaft 44 counter clockwise back to its original position as shown in FIG. 6E so that pawl 58 reengages in needle notch 34c.

Figure 6F:
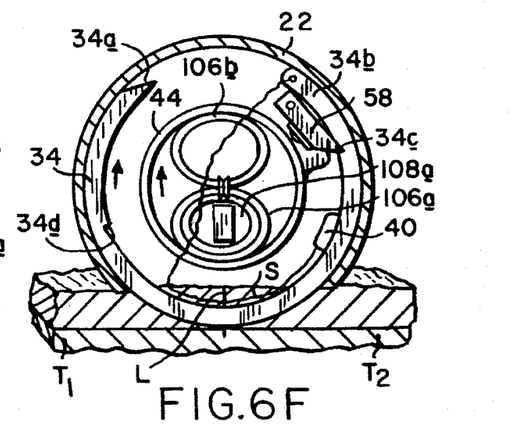
Figure 6G:
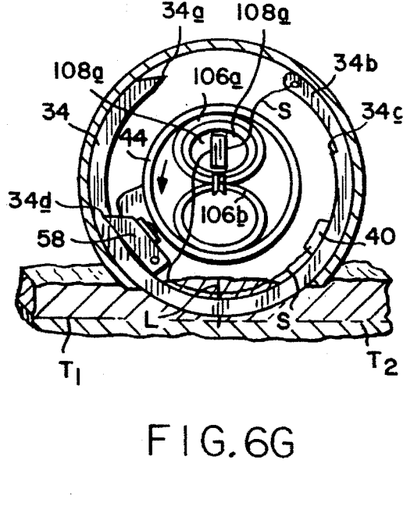
Figure 6H:
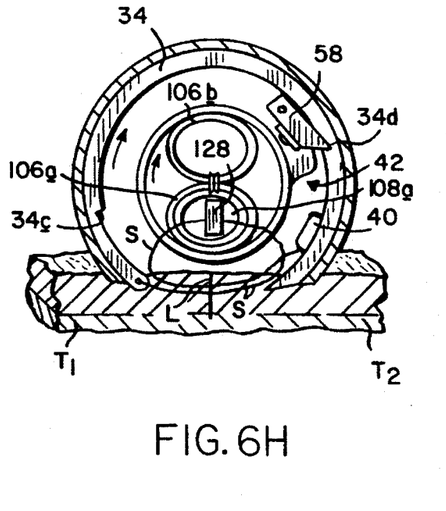

After the formation of the first stitch under the tissues $T_1$ and $T_2$, the instrument is moved along the incision L and the lever 16 is cycled back and forth again as shown in FIGS. 6F and 6G and then moved rearwardly to return the needle 34 to its home position as shown in FIG. 6H. The needle drive mechanism 42 and needle 34 move in the same way described above to produce the first exterior segment or stitch of the suture S. The rotation of the needle 34 through 360° causes the segment of suture S behind needle 34 which has been pulled through the tissues during the first stitch to engage around the hook leg 128 of the extended shuttle 108a as shown in FIGS. 6G and 6H.

Figure 6I:
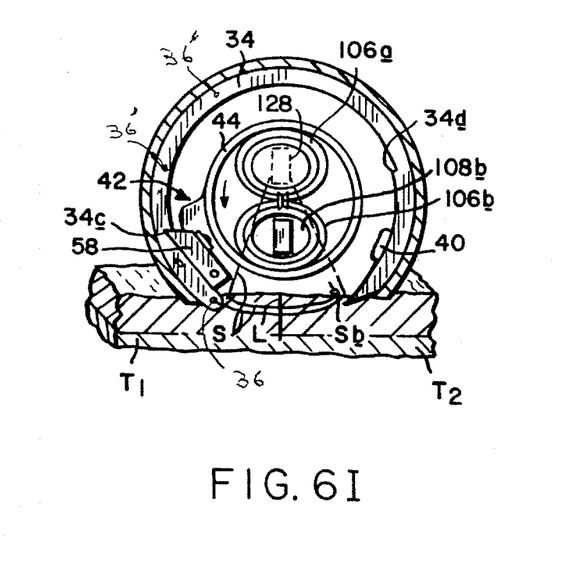

At this point, the surgeon may squeeze trigger 18 which, assuming the trigger linkage positions shown in FIGS. 2 and 4A, will move pinion 84 into engagement with gear 16a. At the same time, the surgeon may move the lever 16 forwardly which causes the drum or pulley 80 to be rotated in the clockwise direction as viewed in FIGS. 2 and 4B. This moves the wire loop 110 in the same direction thereby pulling shuttle 108a toward its retracted position. As the shuttle retracts, it draws the length of suture S wrapped around that shuttle's hook, i.e. the suture segment extending between the first two stitches, along with it into the tube 106a thereby pulling the entire length of suture from the pouch 40 through the tissues $T_1$ and $T_2$ as shown in FIG. 6I. Preferably, a small button $S_b$ is provided at the bitter end of the suture to prevent the suture from pulling completely through the tissues when the suture is first tensioned thusly.

This tension on the suture S also pulls the tissues $T_1$ and $T_2$ together thereby closing the incision L at the site of the first stitch.

Before the shuttle 108a reaches its fully retracted position in tube 106a, the suture is tensioned sufficiently to overcome the bias of spring 132 which maintains hook leg 128 in its laterally extended hooking position shown in FIG. 2 and 5B. Resultantly, the hook leg 128 pivots about pin 126 thereby releasing the loop of suture S inside tube 106a which remains in that tube until the surgeon inserts the next stitch into the tissues $T_1$ and $T_2$. The spring 132 is selected so that the suture is tensioned enough to tighten the stitch without tearing the tissues.

Note from FIG. 6I that after two stitches have been inserted and the suture S tensioned and stored in tube 106a as described above, the needle driver mechanism 42 will have returned to its home position, i.e., the same position it had in FIG. 6E. Also, when the shuttle 108a was retracted during the second stitch, shuttle 108b was extended so that its hook leg 128 is in position to engage suture S during the next stitch.

At this point, the surgeon advances the instrument along the incision L to position the working end of the instrument for the third stitch. When the instrument is properly positioned, the surgeon moves the lever 16 rearwardly, then forwardly and then rearwardly again exactly as described above in connection with FIGS. 6F to 6H. This action will rotate needle 34 through 360° causing the needle 34 to penetrate down through tissue $T_2$ and up through tissue $T_1$, with the suture S following the curved path of the needle through the tissues as described above. In this case, however, the suture material is paid out from the tube 106a in which it was stored during the previous stitch.

As the needle 34 executes its 360° rotation, the segment of suture extending between the second and third stitches is automatically wrapped around the hook leg 128 of the extended shuttle, in this case, shuttle 108b, so that the suture is in position to be engaged by that hook leg when shuttle 108b is retracted.

To complete the third stitch, the surgeon may squeeze trigger 18 which will cause the bracket 82 to tilt about axle 81 in the opposite direction from the tilt when the trigger was first squeezed. This will bring pinion 86 into meshing engagement with gear 16a so that when lever 16 is moved forwardly, drum 80 will be rotated counterclockwise thereby retracting shuttle 108b and extending shuttle 108a so that they occupy their original positions shown in FIG. 2. The retraction of shuttle 108b will cause the exterior segment of suture S extending between tissues $T_1$ and $T_2$ to be pulled into the tube 106b. This tensions the suture and tightens the previous stitches. Before shuttle 108b reaches its retracted position, the tension on the suture becomes sufficient to overcome the bias of spring 132 on shuttle 108b and trips the hook leg 128 of that shuttle to release the suture in tube 106b before the tension on the suture becomes excessive. The third stitch is now complete and the needle 34, driver mechanism 42 and shuttles 128a and 128b are in their original positions shown in FIG. 6A.

The surgeon may continue to advance the instrument along incision L and operate the instrument as described above to insert as many stitches as are needed to completely close the incision L. With each succeeding stitch, the instrument will drive the needle 34 along a curved path through the tissues $T_1$ and $T_2$ exactly as a surgeon would do if he were suturing manually. In this case, however, no needle holders or other tools are required to maneuver the needle. Also, as with manual suturing, the suture material follows the needle along the curved path through the tissues. After each stitch, the suture S is engaged alternately by the hooks of shuttle 108a and shuttle 108b and drawn into the associated tubes 106a and 106b thereby pulling the entire available length of suture through each stitch and applying just the right amount of tension to the suture to close the incision L without tearing tissue. Again, the handling and tensioning of the suture material by the instrument following each stitch more or less emulates the actions carried out by a surgeon when suturing manually.

After the suturing process is completed, the surgeon may cut and tie off the end of the suture in the usual way. The cartridge 14 may then be unplugged from actuator 8 and disposed of or recycled, as desired. With minor cleaning the actuator 8 should be available for re-use with a fresh cartridge relatively quickly.

While the present instrument may be used to insert a single stitch, it would usually be used to insert continuous sutures composed of many stitches because they are the most tedious and time consuming to insert. Also, while we have specifically illustrated a rigid instrument suitable for use in open surgery, the invention is equally applicable to instruments capable of MIS surgery including arthroscopy, laparoscopy, etc. In this event, the working end or tip of the instrument may be made quite small e.g., less than 4 mm diameter, and be positioned at the end of a long, e.g. 300 mm or more, rigid or flexible shaft able to be slid through a cannula in the same manner as other endoscopic surgical instruments.

In the instrument specifically described herein, needle drive shaft 44 is rotated by moving lever 16 rearwardly using the thumb which mode of operation is similar to that of many forceps. It should be understood, however, that the internal gearing could just as well be arranged so that the shaft 44 rotates in response to squeezing a lever or trigger located in front of grip 12 in a manner similar to the operation of a surgical clip applier, for example. Also, in some applications it may be desirable to rotate drive shaft 44 by means of a conventional pneumatic hydraulic or electric reversible rotary actuator or motor (not shown) controlled by a trigger-activated valve or switch.

Still further, while we have described an instrument having a seperable needle/suture cartridge and actuator, the instrument or the actuator 8 could just as well be designed as a single unit which may be reusable or disposable in its entirety.

Also, the described suture S is a spiral stitch. It should be understood that the instrument may also be used to apply other types of sutures customarily used in surgical procedures. For example, by reversing the position of the instrument after each stitch, the incision L may be closed by a mattress suture. Round holes in organs, e.g., in appendix removal, may be closed by a purse string suture.

It will thus be seen that the objects set forth above, among those made apparent from the preceding description, are efficiently attained. Also, since certain changes may be made in the above description without departing from the scope of the invention, it is intended that all matter contained in the above description or shown in the accompanying drawings shall be interpreted as illustrative and not in a limiting sense.

It should also be understood that the following claims are intended to cover all of the generic and specific features in the invention described herein.

We claim:

1. A suturing instrument comprising
    a needle/suture cartridge, said cartridge including
        support means having opposite ends and an axis extending between them;
        a curved suturing needle having a pointed end;
        a suture having one end attached to said needle,
        track means at one end of said support means for supporting said needle for rotational motion about said axis, and
    actuator means for releasably holding the other end of said support means, said actuator means including rotary means releasably engaging and rotating said needle through successive revolutions about said axis in a direction to advance the pointed end of said needle.

2. The instrument defined in claim 1 wherein said curved needle is circular covering an arc greater than 180° and less than 330° leaving a gap between said needle ends.

3. The instrument defined in claim 1 wherein said needle includes interfitting means which interfit with said rotary means when said needle is rotated in said advancing direction.

4. The instrument defined in claim 1 wherein said actuator means comprise an elongated housing having opposite first and second ends;

holding means at said housing first end for releasably holding the other end of said support means;

a needle driver rotatably mounted in said housing, said driver including a portion which extends from said housing first end into driving engagement with said needle, and means adjacent to said housing second end for rotating said driver.

5. The instrument defined in claim 1 wherein the needle also has an end opposite, and said suture one end is attatched to the needle opposite end.

6. The instrument defined in claim 1 wherein the needle also has an opposite end, and the suture one end is attatched to the needle at a location therealong between the needle apex and said opposite end.

7. A suturing instrument for suturing tissue comprising an elongated housing having opposite ends;

a curved suturing needle having a pointed end;

a suture having one end attached to said needle;

support means at one end of the housing for supporting said needle for rotational motion about an axis;

means in said housing for rotating said needle about said axis through successive revolutions, and tensioning means in said housing for engaging and drawing said suture toward the other end of said housing following each revolution of said needle.

8. The instrument defined in claim 7 wherein said needle has circular curvature, and said support means include
  a cylindrical wall,
  means defining a circular track in the cylindrical wall that constrains the needle to follow a circular path about said axis, and
  an aperture in said wall which intercepts said track whereby the pointed end of the needle traverses the aperture during each revolution of the needle so that when the housing one end is placed against tissue so that the aperture faces the tissue, said needle can follow a curved path through the tissue.

9. The instrument defined in claim 7 wherein said means for rotating include a needle driver rotatably mounted in said housing, said driver including a portion which extends into driving engagement with said needle, and motive means at said housing other end for rotating said driver.

10. A suturing instrument comprising a needle/suture cartridge, said cartridge including support means having opposite ends and an axis extending between them;

a curved suturing needle having a pointed end;

a suture having one end attached to said needle, and track means at one end of said support means for supporting said needle for rotational motion about said axis through successive revolutions.

11. A suturing instrument for suturing tissue comprising an elongated housing having opposite ends;

a curved suturing needle having a pointed end;

a suture having one end attached to said needle;

means defining a circular track at one end of the housing for supporting said needle for rotational motion about the track axis, and means in said housing for advancing said needle along said track through at least one revolution about said axis.

12. The instrument defined in claim 11 and further including means in said housing temporarily storing said suture.

13. The instrument defined in claim 11 and further including at least one lumen positioned in said housing substantially parallel to said axis for temporarily storing suture.

* * * * *